United States Patent [19]

Rector et al.

[11] Patent Number: 4,978,670
[45] Date of Patent: Dec. 18, 1990

[54] ANTHELMINTIC QUATERNARYALKYL ACYLHYDRAZONES, METHOD OF USE AND COMPOSITIONS

[75] Inventors: Douglas L. Rector; George A. Conder; Sylvester D. Folz, all of Kalamazoo City, Mich.

[73] Assignee: The Upjohn Company, Kalamazoo, Mich.

[21] Appl. No.: 312,776

[22] PCT Filed: Apr. 3, 1987

[86] PCT No.: PCT/US87/00697
§ 371 Date: Oct. 7, 1988
§ 102(e) Date: Oct. 7, 1988

[87] PCT Pub. No.: WO87/06132
PCT Pub. Date: Oct. 22, 1987

Related U.S. Application Data

[63] Continuation-in-part of Ser. No. 849,039, Apr. 7, 1986, abandoned.

[51] Int. Cl.⁵ .................. A61K 31/44; C07D 213/89; C07D 213/40
[52] U.S. Cl. .................................. 514/345; 514/348; 514/357; 546/261; 546/265

[58] Field of Search ................ 546/261, 265; 514/348, 514/345, 357

[56] References Cited

U.S. PATENT DOCUMENTS 3,993,760 11/1976 Pohlke et al. .................. 424/250
4,087,536 5/1978 Budde et al. .................. 424/273 R

*Primary Examiner*—Mary C. Lee
*Assistant Examiner*—J. A. H. Russell
*Attorney, Agent, or Firm*—William G. Jameson

[57] ABSTRACT

This invention concerns a process for killing internal parasites, especially nematodes, trematodes and cestodes affecting warm blooded animals such as sheep, cattle, swine, goats, dogs, cats, horses and humans as well as poultry by administering an effective amount of a compound of the Formula I.

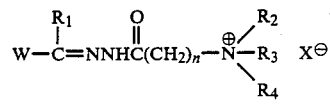

The compounds are readily prepared by conventional chemical reactions.

8 Claims, No Drawings

ANTHELMINTIC QUATERNARYALKYL ACYLHYDRAZONES, METHOD OF USE AND COMPOSITIONS

CROSS-REFERENCE

This is a continuation-in-part of U.S. patent application Ser. No. 06/849,039, filed Apr. 7, 1986, now abandoned.

SUMMARY OF THE INVENTION

This invention pertains to a new method for killing and controlling worms (Helminths), and new formulations for killing and controlling worms in animals and new chemical compounds The invention is more particularly directed to a new method for killing and controlling parasitic worms in animals with certain quaternaryalkyl acylhydrazones to new anthelmintic formulations comprising the same, and to new quaternaryalkyl acylhydrazones.

The anthelmintic quaternaryalkyl acylhydrazones have the general structural formula I.

BACKGROUND OF THE INVENTION

The diseases or groups of diseases described generally as helminthiasis are due to infection of the animal with parasitic worms known as helminths. Helminthiasis and helminthosis are prevalent and may lead to serious economic problems in valuable warm-blooded domestic animals such as sheep, swine, cattle, goats, dogs, cats, horses poultry and man. Among the helminths, the groups of worms known as nematodes trematodes and cestodes cause widespread and often-times serious infections in various species of animals including man. The most common genera of nematodes, trematodes and cestodes infecting the animals referred to above are Dityocaulus, Haemonchus, Trichostrongylus, Ostertagia, Nematodirus, Cooperia, Bunostomum, Oesouhagostomum, Chabertia, Strongyloides, Trichuris, Fasciola, Dicrocoelium, Enterobius, Ascaris, Toxascaris, Toxocara, Ascaridia, Capillaria, Heterakis, Ancylostoma, Uncinaria, Dirofilaria, Onchocerca, Taenia, Moniezia, Dipylidium, Metastrongylus, Triodontophorus, Macracanthorhynchus, Hyostroncylus, and Strongylus. Some of these genera attack primarily the intestinal tract while others, inhabit the stomach, lungs, liver and subcutaneous tissues. The parasitic infections causing helminthiasis and helminthosis lead to anemia, malnutrition, weakness, weight loss, unthriftiness, severe damage to the gastrointestinal tract wall and, if left to run their course, may result in death of the infected animals.

The anthelmintic activity of quaternaryalkyl acylhydrazones has not been previously reported.

DETAILED DESCRIPTION OF THE INVENTION

The quaternaryalkyl acylhydrazones of the invention, including hydrates thereof or pharmaceutically acceptable salts thereof, are represented by Formula I wherein W is selected from the group consisting of
(1) pyridinyl or pyridinyl N-oxide (A);
(2) quinolinyl or quinolinyl N-oxide (B);
(3) thienyl ($D_1$);
(4) furanyl ($D_2$);
(5) pyrrolyl ($D_3$);
(6) 1-methylpyrrolyl ($D_4$);
(7) 1-phenylpyrrolyl ($D_5$);
(8) 1-benzylpyrrolyl ($D_6$);
(9) benzofuranyl ($E_1$);
(10) benzothienyl ($E_2$);
(11) indolyl ($E_3$);
(12) 1-methylindolyl ($E_4$);
(13) 1-phenylindolyl ($E_5$); or
(14) 1-benzylindolyl ($E_6$);
(15) thiazolyl (F);
(16) pyrazolyl (G):
(17) pyrazinyl (H);
(18) 1,2,3-triazolyl (I);
wherein the variable substituents (1)–(18) are optionally substituted with one or two $C_1$–$C_4$ alkyl, preferably $C_1$–$C_3$ alkyl; $C_1$–$C_3$ alkoxy; $C_1$–$C_3$ alkylthio; halo; trifluoromethyl; or hydroxy; with the proviso that only one substituent is hydroxy;
wherein $R_1$ is hydrogen; $C_1$–$C_4$ alkyl; cyclo($C_3$–$C_6$)alkyl optionally substituted with one, 2 or 3 $C_1$–$C_3$ alkyl, preferably cyclo($C_3$–$C_5$)alkyl optionally substituted; phenyl optionally substituted with one, 2 or 3 $C_1$–$C_4$ alkyl, halo, trifluoromethyl, or $C_1$–$C_3$ alkoxy; phenyl($C_1$–$C_3$)alkyl optionally substituted with one, 2 or 3 $C_1$–$C_4$ alkyl, halo, trifluoromethyl, or $C_1$–$C_3$ alkoxy; or 1,3-dioxacyclohexan-5-yl;
wherein n is 1–4; wherein:
(a) $R_2$, $R_3$, $R_4$, being the same or different, are hydrogen., $C_1$–$C_4$ alkyl; phenyl optionally substituted with one, 2 or 3 $C_1$–$C_4$ alkyl or $C_1$–$C_3$ alkoxy; phenyl($C_1$–$C_3$)alkyl; or
(b) two of $R_2$, $R_3$ and $R_4$ are taken together with the nitrogen to form a four to seven-member saturated or partially unsaturated nitrogen-containing ring optionally substituted with phenyl and/or one or two $C_1$–$C_4$ alkyl or $C_1$–$C_4$ alkoxy, said ring optionally containing an oxygen or sulfur atom as a ring member, and the third of $R_2$, $R_3$ and $R_4$ is hydrogen; $C_1$–$C_4$ alkyl; phenyl optionally substituted with one, 2 or 3 $C_1$–$C_4$ alkyl or $C_1$–$C_3$ alkoxy; or phenyl($C_1$–$C_3$)alkyl; or
(c) $R_2$, $R_3$, and $R_4$ are taken together with the nitrogen to form a 6 or 7 member nitrogen-containing aromatic ring optionally substituted with phenyl and/or one or 2 $C_1$–$C_4$ alkyl or $C_1$–$C_3$ alkoxy; or
(d) two of $R_2$, $R_3$ and $R_4$ are taken together with the nitrogen to form an eight to ten-member saturated or partially unsaturated nitrogen-containing bicylic ring optionally substituted with phenyl and/or one or two $C_1$–$C_4$ alkyl or $C_1$–$C_4$ alkoxy, said ring optionally containing an oxygen or sulfur atom as a ring member, and the third of $R_2$, $R_3$ and $R_4$ is hydrogen; $C_1$–$C_4$ alkyl; phenyl optionally substituted with one, 2 or 3 $C_1$–$C_4$ alkyl or $C_1$–$C_3$ alkoxy; or phenyl($C_1$–$C_3$)alkyl; or
(e) $R_2$, $R_3$, and $R_4$ are taken together with the nitrogen to form an eight to ten member nitrogen-containing aromatic bicyclic ring optionally substituted with phenyl and/or one or 2 $C_1$–$C_4$ alkyl or $C_1$–$C_3$ alkoxy; and X is an anion.

Examples of anions are halides, preferably chloride or bromide, acetate, or benzenesulfonate.

Examples of the moiety (-$N^+$-$R_2$,$R_3$,$R_4$) include ammonium, methylammonium, diethylammonium, methyldiphenylammonium, bisphenylmethylammonium, methyl(phenylmethyl)ammonium, methyl(2-phenylethyl)ammonium, 1-methylpiperidinium, 1-ethylmorpholinium, 1-methyl-4-phenyl-1H,2,5,6-tetrahydropyridinium, 2-methoxypyridinium, 4-methylpyridinium, quinolinium, isoquinolinium, 4-methoxy-1-methylindolium, 1-azabicyclo[2,2,2]octanium, 1-methyl-1-azacycloheptatrienium, 2,5-dihydro-1-methylpyrrolidinum, and 1-ethylazetidinium.

$C_--C_-$ means the carbon content of various hydrocarbon-containing moieties is indicated by a prefix designating the minimum and maximum number of carbon atoms in the moiety. Thus ($C_1$-$C_3$) alkyl refers to alkyl of one to 3 carbon atoms, inclusive or methyl, ethyl, propyl, and isopropyl.

Halogen atom (halo) refers to a bromo, chloro, iodo or fluoro atom.

Pharmaceutically acceptable refers to those properties and/or substances which are acceptable to the patient from a pharmacologically-toxicological point of view and to the manufacturing pharmaceutical chemist from a physical-chemical point of view regarding composition, formulation, stability, patient acceptance and bioavailability.

Examples of $C_1$-$C_4$ alkyl are methyl, ethyl, propyl, butyl and isomeric forms thereof. Examples of $C_1$-$C_3$ alkoxy are methoxy, ethoxy, propoxy and isomeric forms thereof.

Examples of phenyl($C_1$-$C_3$)alkyl are benzyl, phenylethyl and phenylpropyl. Examples of phenyl($C_1$-$C_3$)alkyl substituted with one, 2 or 3 $C_1$-$C_4$ alkoxy, halo or trifluoromethyl include 4-chlorobenzyl, 2-chlorophenylethyl, p-tolylethyl, 2-methylbenzyl, 4-methoxybenzyl. Examples of $C_1$-$C_3$ alkylthio include methylthio, ethylthio, and n-propylthio.

Preferred quaternaryalkyl acylhydrazones of Formula I are where W is pyridinyl, i.e. a pyridinyl quaternaryalkyl acylhydrazones (IA).

Preferred $R_1$ include hydrogen, methyl or benzyl;
Preferred n is one;
Preferred $R_2$, $R_3$ and $R_4$ include methyl or the case when $R_2$, $R_3$ and $R_4$ are taken together with the nitrogen to form pyridine;
Preferred X is chloride.

One embodiment of this invention includes, of course, the anthelmintic use and anthelmintic compositions of compounds of Formula I, hydrates thereof or pharmaceutically acceptable salts thereof.

One embodiment of this invention includes, of course, the anti-filaria use and anti-filaria compositions of compounds of Formula I, hydrates thereof or pharmaceutically acceptable salts thereof.

Still another embodiment of this invention are the novel compounds, hydrates thereof or pharmaceutically acceptable salts thereof according to Formula I, IA, IB, ID (including $ID_1$, $ID_2$, $ID_3$, $ID_4$, $ID_5$, $ID_6$), IE (including $IE_1$, $IE_2$, $IE_3$, $IE_4$, $IE_5$, $IE_6$, IF, IG, IH and II).

wherein W, $R_1$, $R_2$, $R_3$, $R_4$, X are described above;
wherein Y and Z, being the same or different, are hydrogen, hydroxy, $C_1$-$C_4$ alkyl, $C_1$-$C_3$ alkoxy, $C_1$-$C_3$ alkylthio, halo, or trifluoromethyl;
G is an oxygen atom, a sulfur atom or a N-V group;
V is hydrogen; $C_1$-$C_3$ alkyl, preferably methyl, phenyl, phenyl-($C_1$-$C_3$)alkyl, preferably benzyl; and
m is 0 or 1.

A is pyridinyl (or pyridinyl N-oxide) optionally substituted with one or two $C_1$-$C_4$ alkyl, $C_1$-$C_3$ alkoxy, $C_1$-$C_3$ alkylthio, halo, trifluoromethyl, or hydroxy;

B is quinolinyl (or quinolinyl N-oxide) optionally substituted with one or two $C_1$-$C_4$ alkyl, $C_1$-$C_3$ alkoxy, $C_1$-$C_3$ alkylthio, halo, trifluoromethyl, or hydroxy;

$D_1$ is thienyl optionally substituted with one or two $C_1$-$C_3$ alkyl, $C_1$-$C_3$ alkoxy, $C_1$-$C_3$ alkylthio, halo, trifluoromethyl, or hydroxy; when G is a sulfur atom;

$D_2$ is furanyl optionally substituted with one or two $C_1$-$C_4$ alkyl, $C_1$-$C_3$ alkoxy, $C_1$-$C_3$ alkylthio, halo, trifluoromethyl, or hydroxy; when G is an oxygen atom;

$D_3$ is pyrrolyl optionally substituted with one or two $C_1$-$C_4$ alkyl, $C_1$-$C_3$ alkoxy, $C_1$-$C_3$ alkylthio, halo, trifluoromethyl, or hydroxy; when G is N-V and V is hydrogen;

$D_4$ is 1-methylpyrrolyl optionally substituted with one or two $C_1$-$C_4$ alkyl, $C_1$-$C_3$ alkoxy, $C_1$-$C_3$ alkylthio, halo, trifluoromethyl, or hydroxy; when G is N-V and V is methyl;

$D_5$ is 1-phenylpyrrolyl optionally substituted with one or two $C_1$-$C_4$ alkyl, $C_1$-$C_3$ alkoxy, $C_1$-$C_3$ alkylthio, halo, trifluoromethyl, or hydroxy; when G is N-V and V is phenyl;

$D_6$ is 1-benzylpyrrolyl optionally substituted with one or two $C_1$-$C_4$ alkyl, $C_1$-$C_3$ alkoxy, $C_1$-$C_3$ alkylthio, halo, trifluoromethyl, or hydroxy; when G is N-V and V is benzyl;

$E_1$ is benzofuranyl optionally substituted with one or two $C_1$-$C_4$ alkyl, $C_1$-$C_3$ alkoxy, $C_1$-$C_3$ alkylthio, halo, trifluoromethyl, or hydroxy; when G is an oxygen atom;

$E_2$ is benzothienyl optionally substituted with one or two $C_1$-$C_4$ alkyl, $C_1$-$C_3$ alkoxy, $C_1$-$C_3$ alkylthio, halo, trifluoromethyl, or hydroxy; when G is a sulfur atom;

$E_3$ is indolyl optionally substituted with one or two $C_1$-$C_4$ alkyl, $C_1$-$C_3$ alkoxy, $C_1$-$C_3$ alkylthio, halo, trifluoromethyl, or hydroxy; when G is N-V and V is hydrogen;

$E_4$ is 1-methylindolyl optionally substituted with one or two $C_1$-$C_4$ alkyl, $C_1$-$C_3$ alkoxy, $C_1$-$C_3$ alkylthio, halo, trifluoromethyl, or hydroxy; when G is N-V and V is methyl;

$E_5$ is 1-phenylindolyl optionally substituted with one or two $C_1$-$C_4$ alkyl, $C_1$-$C_3$ alkoxy, $C_1$-$C_3$ alkylthio, halo, trifluoromethyl, or hydroxy; when G is N-V and V is phenyl; or $E_6$ is 1-benzylinodyl optionally substituted with one or two $C_1$-$C_4$ alkyl, $C_1$-$C_3$ alkoxy, $C_1$-$C_3$ alkylthio, halo, trifluoromethyl, or hydroxy; when G is N-V and V is benzyl;

F is thiazolyl optionally substituted with one or two $C_1$-$C_4$ alkyl, $C_1$-$C_3$ alkoxy, $C_1$-$C_3$ alkylthio, halo, trifluoromethyl, or hydroxy;

G is pyrazolyl optionally substituted with one or two $C_1$-$C_4$ alkyl, $C_1$-$C_3$ alkoxy, $C_1$-$C_3$ alkylthio, halo, trifluoromethyl, or hydroxy;

H is pyrazinyl optionally substituted with one or two $C_1$-$C_4$ alkyl, $C_1$-$C_3$ alkoxy, $C_1$-$C_3$ alkylthio, halo, trifluoromethyl, or hydroxy;

I is triazolyl optionally substituted with one or two $C_1$-$C_4$ alkyl, $C_1$-$C_3$ alkoxy, $C_1$-$C_3$ alkylthio, halo, trifluoromethyl, or hydroxy;

with the overall proviso that only one substituent is hydroxy.

Among the quaternaryalkyl acylhydrazones of Formula I:

1-[[[1-(3-pyridinyl)ethylidene]hydrazino]carbonyl]methyl]-pyridinium chloride (Cpd #2);

1-[[[1-(3-pyridinyl)ethylidene]hydrazino]carbonyl]-propyl]-pyridinium chloride;

Trimethyl [[3-(4-pyridinylmethylene)carbazoyl]methyl-]ammonium chloride (Cpd #6, CA RN 6958-26-5);
(carboxymethyl)trimethylammonium chloride, furfurylidenehydrazide (CA RN 6958-15-2);
(carboxymethyl)trimethylammonium chloride, 2-thienylidenehydrazide (CA RN 6958-28-7);
(Carboxymethyl)trimethylammonium chloride, 2-(pyrrol-2-yl-methylene)hydrazide (Cpd #61, CA 93786-81-3)
are known. See T. Kirchenmayer and F. Kuffner, Monatsh. Chem. 93, 1237–41 (1962); Chem. Abstr. 58:9613C; CAS ON LINE Search (1967 to date); H. Tanaka and O. Yamuchi, Chem. Pharm. Bull (Tokyo) 10, 435–9 (1962); Chem. Abstr. 58, 4498d.

Other known quaternaryalkyl acylhydrazones include (carboxymethyl)trimethylammonium chloride, 5-cyanobenzofurfurylidenehydrazide (CA RN 84223-53-0) and (carboxymethyl)trimethylammonium chloride, 2-[2-[[3-(2-ethoxy-2-oxoethyl)-4-(3-ethoxy-3-oxo-propyl)-1H-pyrrol-2-yl-hydrazide (CA RN 38256-20-1).

The quaternaryalkyl acylhydrazones of the invention (Formula I) are readily prepared by reacting the appropriate heteroaromatic carbonyl compound (ketone or aldehyde) II with the acylhydrazone (known as a Girard Reagent) III (Chart A, Scheme A) or by heating the heteroaromatic carbonyl compound II with hydrazine IV to form the hydrazone intermediate (V) which is then acylated with the halide or anhydride (VI) to form the acylhydrazone (I) (Chart A, Scheme B).

A third route the quaternaryalkyl acylhydrazone (I) is to react the heteroaromatic carbonyl compound II with the acylhydrazide VII to form an intermediate acylhydrazone VIII which is in the final stage reacted with the amine IX to yield I (Chart A, Scheme C).

The condensation reactions of Schemes A, C, and B are carried out in the presence of a suitable solvent; for example, alcohols, ethers, halogenated hydrocarbons, hydrocarbons and include methanol, ethanol, isopropanol, propanol, hexane, tetrahydrofuran, dioxane, and preferably ethanol.

The acylation reaction of Scheme B is carried out in the presence of a nonprotolytic solvent such as ether, halogenated hydrocarbons, hydrocarbons and includes hexane, tetrahydrofuran, dioxane, methylene chloride and preferably methylene chloride.

The starting heteroaromatic ketone and aldehyde intermediates are commercially available or prepared by known methods such as R. C. Frank and C. Weatherbee, J. Am. Chem. Soc., 70, 3482–3 (1948); D. Milstein and J. K. Stille, J. Org. Chem., 44, 1613–1618 (1979); J. E. Parko, B. E. Wagner and R. H. Holm, J. Organometallic Chem., 56, 53 (1963); E. B. Sanders, H. V. Secor and J. I. Seeman, J. Org. Chem., 43, 324–330 (1978).

The hydrazides III and VII are commercially available or readily synthesized by known procedures such as N B. Maheshi et al., J. Indian Chem. Soc., 42, 67–74 (1965).

The following detailed examples procedures describe how to prepare various quaternaryalkyl acylhydrazones of the invention and are to be construed as merely illustrative and not limitations of the preceding disclosure in any way whatsoever. Those skilled in the art will promptly recognize appropriate variations from the procedures both as to reactants as well as to reaction conditions and techniques.

EXAMPLE 1

1-[2-oxo-2-[[2-phenyl-1-(2-pyridinyl)ethylidene]-hydrazino]ethyl]pyridinium chloride. Compound 1

To 5.3 gm (0.03 mole) of Girard Reagent P in 50 ml of methanol is added 5.92 gm (0.03 mole) of benzyl 2-pyridinyl ketone. The mixture is refluxed 2.5 hr. The solvent is evaporated giving a black residue. The residue is slurried in anhydrous ether and the solids collected. The crude solid is crystallized (decolorized with carbon) and then recrystallized twice from ethanol to give 3.55 gm (32%) of the title compound; mp 240.5° (decomp).

Calcd: C, 65.48; H, 5.18; N, 15.28.
Found: C, 64.78; H, 5.26; N, 15.14.

EXAMPLE 2

1-[[[[1-(3-pyridinyl)ethylidene]hydrazino]carbonyl]-methyl]pyridinium chloride. Compound 2

To 5.63 gm (0.03 mole) of Girard's Reagent P in 50 ml of anhydrous methanol is added 3.63 gm (0.03 mole) of 3-acetylpyridine. The solution is refluxed 3 hr and cooled. The solvent is evaporated The residue is slurried in 100 ml of anhydrous ether and filtered. The crude product is recrystallized from absolute ethanol to afford 6.18 gm (71%) of the title compound; mp 237.2° (decomp).

Calcd: C, 57.83; H, 5.16; N, 19.28.
Found: C, 57.64; H, 5.13; N, 19.36.

EXAMPLE 3

1-[[[[1-(2-pyridinyl)ethylidene]hydrazino]carbonyl]methyl]pyridinium chloride. Compound 3

Following the general method of Example 2 and making non-critical variations, 5.63 gm (0.03 mole) of Girard's Reagent P and 3.63 gm (0.03 mole) of 2-acetylpyridine yield 5.70 gm (65%) of the title compound; mp 183.7° (decomp).

Calcd: C, 57.83; H, 5.16; N, 19.28; Cl, 12.20.
Found: C, 58.27; H, 5.44; N, 19.08.

1-[[[[1-(2-pyridinyl)ethylidene]hydrazinocarbonyl]-methyl]-pyridinium chloride is remade, with a scape-up of 7.5x, using the above procedure to give 17.5 gm (26%) in three crops.

Found: C, 54.61; H, 4.99; N, 18.29; Cl, 12.09; mp 143°–144°.
Found: C, 53.99; H, 5.22; N, 17.32; Cl, 10.71; mp 142°–143°. C, 55 27; H, 5.09; N, 19.18; Cl, 11.33; mp 141°–143°.

EXAMPLE 4

Trimethyl [[3-[1-(3-pyridinyl)ethylidene]carbazoyl]-ammonium chloride monohydrate. Compound 4

To 5.3 gm (0.03 mole) of Girard's Reagent T in 100 ml methanol is added 3.63 gm (0.03 mole) of 3-acetylpyridine. The reaction mixture is refluxed 6 hr and cooled to give crystals. The product is collected and recrystallized from methanol to afford 6.08 gm (70%) of the title compound; mp 199.4° (decomp)

Calcd: C, 49.91; H, 7.28; N, 19.41.
Found: C, 50.24; H, 7.23; N, 19.63.

EXAMPLE 5

Trimethyl [[3-[1-(4-pyridinyl)ethylidene]carbazoyl]methyl]ammonium chloride. Compound 5

Following the general method of Example 4 and making non-critical variations, 5.03 gm (0.03 mole) of Girard's Reagent T and 3.63 gm (0.03 mole) of 4-acetylpyridine yield 3.76 gm (45%) of the title compound; mp 213° (decomp).

Calcd: C, 51.19; H, 7.18; N, 19.91.
Found: C, 50.92; H, 7.05; N, 19.73.

EXAMPLE 6

Trimethyl [[3-(4-pyridinylmethylene)carbazoyl]methyl]ammonium chloride. Compound 6

Following the general method of Example 4 and making non-critical variations, 5 03 gm (0.03 mole) of Girard's Reagent T and gm (0.03 mole) of 4-pyridinecarboxaldehyde yield 4.35 gm (56%) of the title compound; mp 220° (decomp).

Calcd: C, 51.46; H, 6.63; N, 21.83.
Found: C, 51.85; H, 6.90; N, 21.94.

EXAMPLE 7

Trimethyl [[3-[1-(2 pyridinyl)ethylidene]carbazoyl]-methyl]ammonium chloride. Compound 7.

Following the general method of Example 4 and making non-critical variations, 5.03 gm (0.03 mole) of Girard's Reagent T and 3.63 gm (0.03 mole) of 2-acetylpyridine yield 2.05 gm (24%) of the title compound; mp 208.2° (decomp).

Calcd: C, 49.91; H, 7.28; N, 19.41.
Found: C, 50.34; H, 7.49; N, 19.54.

Employing the above procedure, using a 5.2x scale-up gives 25.74 gm (58%) of the title compound, mp 190.0°.

EXAMPLE 8

Dimethyl[[3-(2-thienylmethylene)carbazoyl]methyl]-ammonium chloride. (Compound 18)

A mixture of 7.68 gm (0.05 mole) Girard Reagent D, 5.61 gm (0.05 mole) 2-thiophenecarboxaldehyde, 3 drops of concentrated hydrochloric acid and 250 ml of absolute ethanol is refluxed 12 hr. The solvent is evaporated. The residue is dissolved in absolute ethanol, treated with Darco decolorizing carbon and filtered. The filtrate is chilled. The solid which deposits is collected, washed with ether and dried to give 8.1 gm (65%) of the title compound having a melting point of 207.9° C. with decomposition.

Calcd: C, 43.63; lf, 5.70; N, 16.96.
Found: C, 51.85; lf, 5.72; N, 17.08.

The compounds prepared according to Examples 1–8 are tabulated in Table A along with other illustrative compounds of the invention prepared following the general procedure/example indicated (1–8) and making non-critical variations, except starting with the appropriate ketone (II) and aryl hydrazide/carbazate (III).

The quaternaryalkyl acylhydrazones of this invention are effective against worms, particularly parasitic worms of valuable domestic warm-blooded animals including helminth parasites in ovines (sheep) and bovines (cattle) but more particularly the filarial parasites of warm-blooded animals including dogs and man.

Although non of the pyridinyl quarternaryalkyl acylhydrazones of this invention tested have demonstrated significant activity against *Nematospiroides dubius* in mice, observations in sheep experimentally infected with *Haemonchus contortus* in accordance with Procedure I, generally confirm anthelmintic activity upon oral administration as set forth in Table I. Quaternaryalkyl acylhydrazones which are toxic are expected to exhibit anthelmintic activity at a lower non-toxic dose.

Further observations in male Mongolian jirds infected with *Brugia pahangi* and *Dipetalonema viteae* (Procedure II) confirm macro- and microfilaricidal activity of an quaternaryalkyl acylhydrazone of this invention (Table II).

PROCEDURE NO. I

In individual experiments all sheep are treated identically, however non-critical variations occur between experiments All of the sheep used in this procedure are treated twice with levamisole hydrochloride orally at 8 mg/kg or once each with ivermectin parenterally at 200 $\mu$g/kg and levamisole hydrochloride orally at 8 mg/kg. The second treatment in each case is administered 4–7 days after the first treatment. Two weeks after the second treatment all sheep are inoculated per os with ~3,500 to ~7,500 infective larvae of *H. contortus*. Rectal fecal samples are taken from each sheep 26–41 days post-inoculation (PI). and these samples are examined for eggs of *H. contortus* using the McMaster counting chamber technique. All sheep harboring good infections of *H. contortus* are randomly allocated to a treatment group; those which do not exhibit suitable infections are dropped from the study. One–three days later on days 27–42 PI each sheep remaining in the study (excluding the nontreated controls) is treated with a test compound (orally at 100 mg/kg unless indicated otherwise) or a standard (levamisole hydrochloride orally at 8 mg/kg) or is used as an untreated control. All sheep received food and water ad lib throughout the experiment.

Prior to administration, all solid compounds are finely ground using a mortar and pestle. Oral compounds are suspended in 20.30 ml of sterile vehicle #98 (each ml contains: carboxymethylcellulose—10 mg, polysorbate 80–84 mg, propylparaben—0.42 mg) using a sonicator and administered along with a tap water wash via a stomach tube. All test compounds are given to a single sheep. Two or more sheep are treated with levamisole hydrochloride and five are used as non-treated controls. All animals are monitored for signs of toxicity following treatment.

The sheep are sacrificed 7–12 days after treatment (days 35–49 PI), and the abomasum is ligated and removed from each sheep. Each abomasum is longitudinally sectioned and rinsed into an 80 mesh sieve. Sieve contents are collected in individual containers and fixed in formol-alcohol. Later each sample is transferred to a 1000 or 2000 ml beaker and the volume brought to 400–1000 ml with tap water. The total number of worms in a 40–100 ml aliquot (10%) is determined. When no worms are found in the 10% aliquot, the entire sample is examined. Total worm number/sheep and percentage clearance for each treatment are calculated. Percentage clearance for a particular test compound in a given trial is determined according to the following formula:

Percentage Clearance = [(Mean number of worms recovered
(Test Compound)       from nontreated control sheep −
                      Number of worms recovered from
                      treated sheep)/Mean number
                      of worms recovered from
                      nontreated control sheep] × 100.

Sheep which die within 24 hr following treatment are not examined for worms, while any that die between 24 hr post-treatment and necropsy are examined in an identical manner as that described above. The results of various trials are combined and reported in Table I as percentage clearance.

PROCEDURE NO. II

Antifilarial Evaluation

Test compound is evaluated for macro- and microfilaricidal activity against *Brugia pahangi* and *Dipetalonema viteae* in male jirds (*Merioner unguiculatus*) weighing 50–60 gm. *Brugia pahangi* is maintained by alternating passage through beagles and *Aedes aegypti* (selected Liverpool strain), while *D. viteae* is cyclically maintained in jirds and the soft tick, *Ornithodoros tartakovsky* as described by McCall (C. J. Entomol. 16:283–293, 1981). Prior to the start of the experiment each jird receives 5 male and 5 female, adult *D. viteae* by subcutaneous transplantation. One to 2 weeks later, 10 male and 10 female *B. pahangi* are transplanted into the peritoneal cavity of each animal (Suswillo and Denham, J. Parasitol. 63:591, 1977). One week later jirds are randomly allocated to treatment groups (3 animals/treated group and 6 animals/nontreated control group). On the following Monday (day 0). pretreatment microfilaremia levels (*D. viteae*) are determined by spreading a 20 cmm sample of ocular blood over a 20×15 mm area of a slide in a drop of water. The slide is dried overnight and then stained with Giemsa. Microfilariae are counted to a total of at least 200 per slide and the number of fields noted (a minimum of 5 fields must be counted). Since there are 1.43 cmm per 10 fields on the calibrated scope, the number of microfilariae per cmm can be calculated.

On day 0, dosing is also initiated. The compound, suspended in hydroxyethylcellulose (0 5%) and Tween 80 (0.1%). is administered at 100 mg/kg/day for 5 days by subcutaneous injection. Microfilaremia levels are determined on days 4 and 56 posttreatment as described above On∼day 60 posttreatment all jirds are sacrificed to determine the effects of the drug on adults of *D. viteae* and *B. pahangi* in the skin and peritoneal cavity, respectively. Live worms are identified to species, noted as to sex, and counted. The number of dead and/or encapsulated worms also is recorded. A reduction of ≧80% in microfilaremia or ≧50% in adult worm burden compared to pretreatment microfilaremia or nontreated control worm burden, respectively, is considered to be significant activity.

The results for an acylhydrazone of Formula I is set forth in Table II.

DETAILED DESCRIPTION (cont'd)

The quaternaryalkyl acylhydrazones of Formula I can be used as the pure compounds or as mixtures of pure compounds but for practical reasons the compounds are preferably formulated as anthelmintic compositions and administered as a single or multiple dose, alone or in combination with other anthelmintics (e.g. avermectins, benzimidazoles, levamisole, praziquantel, etc.). For example, aqueous or oil suspensions can be administered orally, or the compounds can be formulated with a solid carrier for feeding. Furthermore, an oil suspension can be converted into an aqueous emulsion by mixing with water and injecting the emulsion intra muscularly, subcutaneously or into the peritoneal cavity. In addition, the active compound(s) can be administered topically to the animal in a conventional pour-on formula.

Pure compounds, mixtures of the active compounds, or combinations thereof with a solid carrier can be administered in the animal's food, or administered in the form of tablets, pills, boluses, wafers, pastes, and other conventional unit dosage forms, as well as sustained-/controlled release dosage forms which deliver the active compound over an extended period of days, weeks or months. All of these various forms of the active compounds of this invention can be prepared using physiologically acceptable carriers and known methods of formulation and manufacture.

Representative solid carriers conveniently available and satisfactory for physiologically acceptable, unit dosage formulations include corn starch, powdered lactose, powdered sucrose, talc, stearic acid, magnesium stearate, finely divided bentonite, and the like. The active agent can be mixed with a carrier in varying proportions from, for example, about 0.001 percent by weight in animal feed to about 90 or 95 percent or more in a pill or capsule In the latter form, one might use no more carrier than sufficient to bind the particles of active compound.

In general, the compounds can be formulated in stable powders or granules for mixing in an amount of feed for a single feeding or enough feed for one day and thus obtain therapeutic efficacy without complication. It is the prepared and stored feeds or feed premixes that require care. A recommended practice is to coat a granular formulation to protect and preserve the active ingredient. A prepared hog-feed containing about 0.2 percent of the active compound will provide a dosage of about 100 mg per kg body weight for each 100 lb pig in its daily ration.

A solid diluent carrier need not be a homogeneous entity, but mixtures of different diluent carriers can include small proportions of adjuvants such as water; alcohols; protein solutions and suspensions like skimmed milk; edible oils; solutions, e.g., syrups; and organic adjuvants such as propylene glycols, sorbitol, glycerol, diethylcarbonate, and the like.

The solid carrier formulations of the inventions are conveniently prepared in unit dosage forms, to facilitate administration to animals. Accordingly, several large boluses (about 20 g weight) amounting to about 54 g of active compound would be required for a single dosage to a 900 lb horse at a dosage rate of 50 mg/kg of body weight. Similarly, a 60 lb lamb at a dosage rate of 100 mg/kg of body weight would require a pill, capsule, or bolus containing about 2.7 g of active compound. A small dog, on the other hand, weighing about 20 lbs. would require a total dosage of about 225 mg st a dosage rate of 25 mg/kg of body weight. The solid, unit dosage forms can be conveniently prepared in various sizes and concentrations of active ingredient, to accommodate treatment of the various sizes of animals that are parasitized by worms.

Liquid formulations can also be used. Representative liquid formulations include aqueous (including isotonic saline) suspensions, oil solutions and suspensions, and oil in water emulsions. Aqueous suspensions are obtained by dispersing the active compound in water preferably including a suitable surface-active dispersing agent such as cationic anionic, or non-ionic surface-active agents. Representative suitable ones are polyoxyalkylene derivatives of fatty alcohols and of sorbitan esters, and glycerol and sorbitan esters of fatty acids. Various dispersing or suspending agents can be included and representative ones are synthetic and natural gums, tragacanth, acacia, alginate, dextran, gelatin, sodium carboxymethylcellulose methylcellulose, sodium polyvinylpyrrolidone, and the like. The proportion of the active compound in the aqueous suspensions of the invention can vary from about 1 percent to about 20 percent or more.

Oil solutions are prepared by mixing the active compound and an oil, e.g. an edible oil such as cottonseed oil, peanut oil, coconut oil, modified soybean oil, and sesame oil. Usually, solubility in oil will be limited and oil suspensions can be prepared by mixing additional finely divided compound in the oil.

Oil in water emulsions are prepared by mixing and dispersing an oil solution or suspension of the active compound in water preferably aided by surface-active agents and dispersing or suspending agents as indicated above.

In general, the formulations of this invention are administered to animals so as to achieve therapeutic or prophylactic levels of the active compound.

In other animals, and for other kinds of parasitic worms, definitive dosages can be proposed. Contemplated are dosage rates of about 1 mg to about 800 mg/kg of body weight. A preferred, contemplated range of dosage rates is from about 5 mg to about 400 mg/kg of body weight. In this regard, it should be noted that the concentration of active compound in the formulation selected for administration is in many situations not critical. One can administer a larger quantity of a formulation having a relatively low concentration and achieve the same therapeutic or prophylactic dosage as a relatively small quantity of a relatively more concentrated formulation. More frequent small dosages will likewise give results comparable to one large dose. One can also administer a sustained release dosage system (protracted delivery formulation) so as to provide therapeutic and/or prophylactic dosage amounts over an extended period Unit dosage forms in accordance with this invention can have anywhere from less than 1 mg to 500 g of active compound per unit.

Although the anthelmintic agents of this invention will find their primary use in the treatment and/or prevention of helminth parasitisas in domesticated animals such as sheep, cattle, horses, dogs, swine goats and poultry, they are also effective in treatment that occurs in other warm blooded animals including man. The optimum amount to be employed for best results will, of course, depend upon the particular quaternaryalkyl acylhydrazone compound employed, species of animal to be treated, the regimen treatment and the type and severity of helminth infection. Generally good results are obtained with compounds of Formula I by the oral or parenteral route of administration of about 1 to 200 mg/kg of animal body weight (such total dose being given at one time, in a protracted manner or in divided doses over a short period of time such as 1–4 days). The technique for administering these materials to animals are known to those skilled in the veterinary and medical fields.

It is contemplated that the quaternaryalkyl acylhydrazones of Formula I can be used in the treatment and/or prevention of Dirofilaria in dogs at a dose of from 1 mg/kg to 100 mg/kg of body weight upon oral and/or parenteral daily/weekly or bimonthly administration depending upon the particular compound employed and the type and severity of infection.

It is also contemplated that the quaternaryalkyl acylhydrazones of Formula I can be used to treat various helminth diseases in humans, including those caused by Ascaris, Enterobius, Ancylostoma, Trichuris, Stronzvloides, Fasciola, Taenia, and/or Onchocerca or other filaria at a dose of from 1 mg/kg to 300 mg/kg of body weight upon oral and/or parenteral administration.

DEFINITIONS

The definitions and explanations below are for the terms as used throughout the entire patent application including both the specification and claims.

All temperatures are in degrees Celsius.

TLC refers to thin-layer chromatography.

Brine refers to an aqueous saturated sodium chloride solution.

When solvent pairs are used, the ratio of solvents used are volume/volume (v/v).

TABLE A $$W-\underset{R_1}{C}=NNHC(CH_2)_n-\overset{R_2}{\underset{R_4}{\overset{\oplus}{N}}}-R_3 \quad X^{\ominus} \qquad I$$

| C | W | $R_1$ | n | $R_2$ | $R_3$ | $R_4$ | $X^-$ | MP, °C. | P | H |
|---|---|---|---|---|---|---|---|---|---|---|
| 1 | 2-pyridinyl | PhCH$_2$ | 1 | 1-pyridinyl | | | Cl | 240.5d | 1 | — |
| 2 | 3-pyridinyl | CH$_3$ | 1 | 1-pyridinyl | | | Cl | 237.2d | 2 | — |
| 3 | 2-pyridinyl | CH$_3$ | 1 | 1-pyridinyl | | | Cl | 183.7d | 2 | — |
| 4 | 3-pyridinyl | CH$_3$ | 1 | CH$_3$ | CH$_3$ | CH$_3$ | Cl | 199.4d | 4 | — |
| 5 | 4-pyridinyl | CH$_3$ | 1 | CH$_3$ | CH$_3$ | CH$_3$ | Cl | 213d | 4 | — |
| 6 | 4-pyridinyl | H | 1 | CH$_3$ | CH$_3$ | CH$_3$ | Cl | 220d | 4 | — |
| 7 | 2-pyridinyl | CH$_3$ | 1 | CH$_3$ | CH$_3$ | CH$_3$ | Cl | 208.2d | 4 | — |
| 8 | 3-thienyl | H | 1 | 1-pyridinyl | | | Cl | 244.2d | 1 | — |
| 9 | 3-thienyl | H | 1 | CH$_3$ | CH$_3$ | CH$_3$ | Cl | 214.6 | 1 | — |
| 10 | 3-thienyl | H | 1 | CH$_3$ | CH$_3$ | H | Cl | 182.1d | 1 | — |
| 11 | 3-methyl-2-thienyl | CH$_3$ | 1 | 1-pyridinyl | | | Cl | 247.8d | 1 | — |
| 12 | 3-methyl-2-thienyl | CH$_3$ | 1 | CH$_3$ | CH$_3$ | CH$_3$ | Cl | 209.4d | 1 | — |
| 13 | 2-pyridinyl | CH$_3$ | 1 | CH$_3$ | CH$_3$ | H | Cl | 219.6d | 1 | — |
| 14 | 3-pyridinyl | CH$_3$ | 1 | CH$_3$ | CH$_3$ | H | Cl | 216.1d | 1 | — |
| 15 | 4-pyridinyl | CH$_3$ | 1 | CH$_3$ | CH$_3$ | H | Cl | 180.1 | 1 | — |

TABLE A-continued $$W-\underset{\underset{R_1}{|}}{C}=NNHC(CH_2)_n-\overset{\oplus}{\underset{\underset{R_4}{\backslash}}{N}}\!\!\overset{R_2}{\underset{R_3}{/}} \quad X^\ominus \qquad I$$

| C | W | R₁ | n | R₂ | R₃ | R₄ | X⁻ | MP, °C | P | H |
|---|---|---|---|---|---|---|---|---|---|---|
| 16 | 4-pyridinyl | CH₃ | 1 | 1-pyridinyl | | | Cl | 272.1d | 1 | — |
| 17 | 2-thienyl | H | 1 | 1-pyridinyl | | | Cl | 236.1d | 1 | — |
| 18 | 2-thienyl | H | 1 | CH₃ | CH₃ | H | Cl | 207.9d | 8 | — |
| 19 | 5-chloro-2-thienyl | CH₃ | 1 | 1-pyridinyl | | | Cl | 197.6d | 8 | — |
| 20 | 5-chloro-2-thienyl | CH₃ | 1 | CH₃ | CH₃ | CH₃ | Cl | 192.2d | 8 | — |
| 21 | 5-chloro-2-thienyl | CH₃ | 1 | CH₃ | CH₃ | H | Cl | 183.8 | 8 | — |
| 22 | 5-bromo-2-thienyl | CH₃ | 1 | 1-pyridinyl | | | Cl | 231.5d | 8 | — |
| 23 | 2,5-dichloro-3-thienyl | CH₃ | 1 | 1-pyridinyl | | | Cl | 241.4 | 8 | — |
| 24 | 2,5-dichloro-3-thienyl | CH₃ | 1 | CH₃ | CH₃ | CH₃ | Cl | 220.8 | 8 | — |
| 25 | 2,5-dimethyl-3-thienyl | CH₃ | 1 | 1-pyridinyl | | | Cl | 248.8d | 8 | — |
| 26 | 2,5-dimethyl-3-thienyl | CH₃ | 1 | CH₃ | CH₃ | CH₃ | Cl | 206.7d | 8 | — |
| 27 | 5-methyl-2-thienyl | CH₃ | 1 | 1-pyridinyl | | | Cl | 225.7d | 8 | — |
| 28 | 5-methyl-2-thienyl | CH₃ | 1 | CH₃ | CH₃ | CH₃ | Cl | 196.7 | 8 | — |
| 29 | 5-methyl-2-thienyl | CH₃ | 1 | CH₃ | CH₃ | H | Cl | 218.5d | 8 | — |
| 30 | 2-thienyl | CH₃ | 1 | 1-pyridinyl | | | Cl | 216.3d | 8 | — |
| 31 | 2-thienyl | CH₃ | 1 | CH₃ | CH₃ | CH₃ | Cl | 187.8d | 8 | — |
| 32 | 2-thienyl | CH₃ | 1 | CH₃ | CH₃ | H | Cl | 198.2 | 8 | — |
| 33 | 3-thienyl | CH₃ | 1 | 1-pyridinyl | | | Cl | 233.4d | 8 | — |
| 34 | 3-thienyl | CH₃ | 1 | CH₃ | CH₃ | CH₃ | Cl | 205.8 | 8 | — |
| 35 | 3-thienyl | CH₃ | 1 | CH₃ | CH₃ | H | Cl | 261.2d | 8 | — |
| 36 | 4-methyl-2-thienyl | CH₃ | 1 | 1-pyridinyl | | | Cl | 225.2 | 8 | — |
| 37 | 4-methyl-2-thienyl | CH₃ | 1 | CH₃ | CH₃ | CH₃ | Cl | 190.0 | 8 | — |
| 38 | 4-methyl-2-thienyl | CH₃ | 1 | CH₃ | CH₃ | H | Cl | 231.2d | 8 | — |
| 39 | 3-methyl-2-thienyl | H | 1 | 1-pyridinyl | | | Cl | 236.8d | 8 | — |
| 40 | 3-methyl-2-thienyl | H | 1 | CH₃ | CH₃ | CH₃ | Cl | 231.2d | 8 | — |
| 41 | 5-methyl-2-furanyl | CH₃ | 1 | 1-pyridinyl | | | Cl | 214.2d | 8 | + |
| 42 | 5-methyl-2-furanyl | CH₃ | 1 | CH₃ | CH₃ | CH₃ | Cl | 190.7d | 8 | + |
| 43 | 2,5-dimethyl-3-furanyl | CH₃ | 1 | 1-pyridinyl | | | Cl | 190.0d | 8 | + |
| 44 | 2,5-methyl-3-furanyl | CH₃ | 1 | CH₃ | CH₃ | CH₃ | Cl | 197.4d | 8 | + |
| 45 | 4-methyl-2-thienyl | CH₃ | 1 | CH₃ | CH₃ | H | Cl | 233.0d | 8 | — |
| 46 | 3-methyl-2-thienyl | H | 1 | CH₃ | CH₃ | H | Cl | 235.7 | 8 | + |
| 47 | 2-thienyl | c-C₃H₅ | 1 | 1-pyridinyl | | | Cl | 207.0d | 8 | — |
| 48 | 2,4-dimethyl-5-thiazolyl | CH₃ | 1 | CH₃ | CH₃ | CH₃ | Cl | 189.2d | 1 | + |
| 49 | 2,4-dimethyl-5-thiazolyl | CH₃ | 1 | CH₃ | CH₃ | H | Cl | 175.8d | 1 | + |
| 50 | 5-methyl-1-phenyl-4-pyrazolyl | CH₃ | 1 | 1-pyridinyl | | | Cl | 214.5d | 1 | — |
| 51 | 5-methyl-2-thienyl | H | 1 | 1-pyridinyl | | | Cl | 228.8d | 8 | — |
| 52 | 5-methyl-2-thienyl | H | 1 | CH₃ | CH₃ | CH₃ | Cl | 221.5d | 8 | + |
| 53 | 5-methyl-2-thienyl | H | 1 | CH₃ | CH₃ | H | Cl | 225.2d | 8 | + |
| 54 | 5-methyl-2-furanyl | H | 1 | 1-pyridinyl | | | Cl | 226.2d | 8 | + |
| 55 | 5-methyl-2-furanyl | H | 1 | CH₃ | CH₃ | CH₃ | Cl | 239.1d | 8 | — |
| 56 | 5-methyl-2-furanyl | H | 1 | CH₃ | CH₃ | H | Cl | 225.2d | 8 | — |
| 57 | 3-benzothienyl | CH₃ | 1 | 1-pyridinyl | | | Cl | 246.2d | 8 | + |
| 58 | 3-benzothienyl | CH₃ | 1 | CH₃ | CH₃ | CH₃ | Cl | 236.0d | 8 | + |
| 59 | 3-benzothienyl | CH₃ | 1 | CH₃ | CH₃ | H | Cl | 244.2d | 8 | — |
| 60 | 2-pyrrolyl | H | 1 | 1-pyridinyl | | | Cl | 215–218d | 1 | + |
| 61 | 2-pyrrolyl | H | 1 | CH₃ | CH₃ | CH₃ | Cl | 224–226d | 1 | — |
| 62 | 2-pyrrolyl | H | 1 | CH₃ | CH₃ | H | Cl | 230–231d | 1 | — |
| 63 | 1-methyl-2-pyrrolyl | H | 1 | 1-pyridinyl | | | Cl | 228–229d | 1 | — |
| 64 | 1-methyl-2-pyrrolyl | H | 1 | CH₃ | CH₃ | CH₃ | Cl | 239–241d | 1 | — |
| 65 | 5-bromo-2-thienyl | CH₃ | 1 | CH₃ | CH₃ | CH₃ | Cl | 203.8d | 8 | — |
| 66 | 5-bromo-2-thienyl | CH₃ | 1 | CH₃ | CH₃ | H | Cl | 198.6d | 8 | + |
| 67 | 4-quinolinyl | H | 1 | 1-pyridinyl | | | Cl | 249.8d | 1 | — |
| 68 | 4-quinolinyl | H | 1 | CH₃ | CH₃ | CH₃ | Cl | 216.3d | 1 | + |
| 69 | 1-methylindol-3-yl | H | 1 | 1-pyridinyl | | | Cl | 196.0d | 1 | + |
| 70 | 1-methylindol-3-yl | H | 1 | CH₃ | CH₃ | H | Cl | 253.0d | 1 | — |
| 71 | 1-methylindol-3-yl | H | 1 | CH₃ | CH₃ | H | Cl | 253.0d | 1 | — |
| 72 | 2-pyrazinyl | CH₃ | 1 | 1-pyridinyl | | | Cl | 248.1d | 2 | + |
| 73 | 2-pyrazinyl | CH₃ | 1 | CH₃ | CH₃ | CH₃ | Cl | 249.5d | 1 | — |
| 74 | 2-pyrazinyl | CH₃ | 1 | CH₃ | CH₃ | H | Cl | 220.6d | 1 | — |
| 75 | 2-thienyl | C₂H₅ | 1 | CH₃ | CH₃ | H | Cl | 189.8 | 8 | + |
| 76 | 2-thienyl | C₃H₇ | 1 | CH₃ | CH₃ | H | Cl | 166.4 | 1 | + |
| 77 | 5-methyl-1-phenyl-4-pyrazolyl | CH₃ | 1 | CH₃ | CH₃ | CH₃ | Cl | 150.7 | 1 | + |
| 78 | 3-methyl-2-pyrazinyl | CH₃ | 1 | 1-pyridinyl | | | Cl | 230.5d | 1 | + |
| 79 | 3-methyl-2-pyrazinyl | CH₃ | 1 | CH₃ | CH₃ | CH₃ | Cl | 217.6d | 1 | — |
| 80 | 3-methyl-2-pyrazinyl | CH₃ | 1 | CH₃ | CH₃ | H | Cl | 221.5d | 1 | — |
| 81 | 2-(4-chlorophenyl)-4-methyl-(2H)-1,2,3-triazolyl | CH₃ | 1 | 1-pyridinyl | | | Cl | 238.5d | 2 | — |
| 82 | 2-(4-chlorophenyl)-4-methyl-(2H)-1,2,3-triazolyl | CH₃ | 1 | CH₃ | CH₃ | CH₃ | Cl | 230.0d | 2 | — |
| 83 | 2-(4-chlorophenyl)-4-methyl-(2H)-1,2,3-triazolyl | CH₃ | 1 | CH₃ | CH₃ | H | Cl | 257.9d | 2 | — |

TABLE I
| | H. Contortus | |
|---|---|---|
| | % Clearance | |
| Compound No. | P.O | I.P |
| 1 | N.T. | N.T |
| 2 | 40.3 | N.T |
| 3 | 27.0 | N.T |
| 4 | 0 | N.T |
| 5 | 0 | N.T |
| 6 | N.T. | N.T |
| 7 | N.T. | N.T |
TABLE II
Chemotherapeutic activity of Compound 1 in jirds (*M. unguiculatus*) Against *D. viteae* and *B. pahangi*.
| | Dose | | % Filarial Reduction of: | | | |
|---|---|---|---|---|---|---|
| | mg/kg/day | Admin. | Macrofil. | | Microfil. | |
| Cmpd.# | x5 | Route | BpL5 | DvL5 | 4 days | 56 days |
| 1 | 100 | SC | 100 | 0 | 40 | 100 |
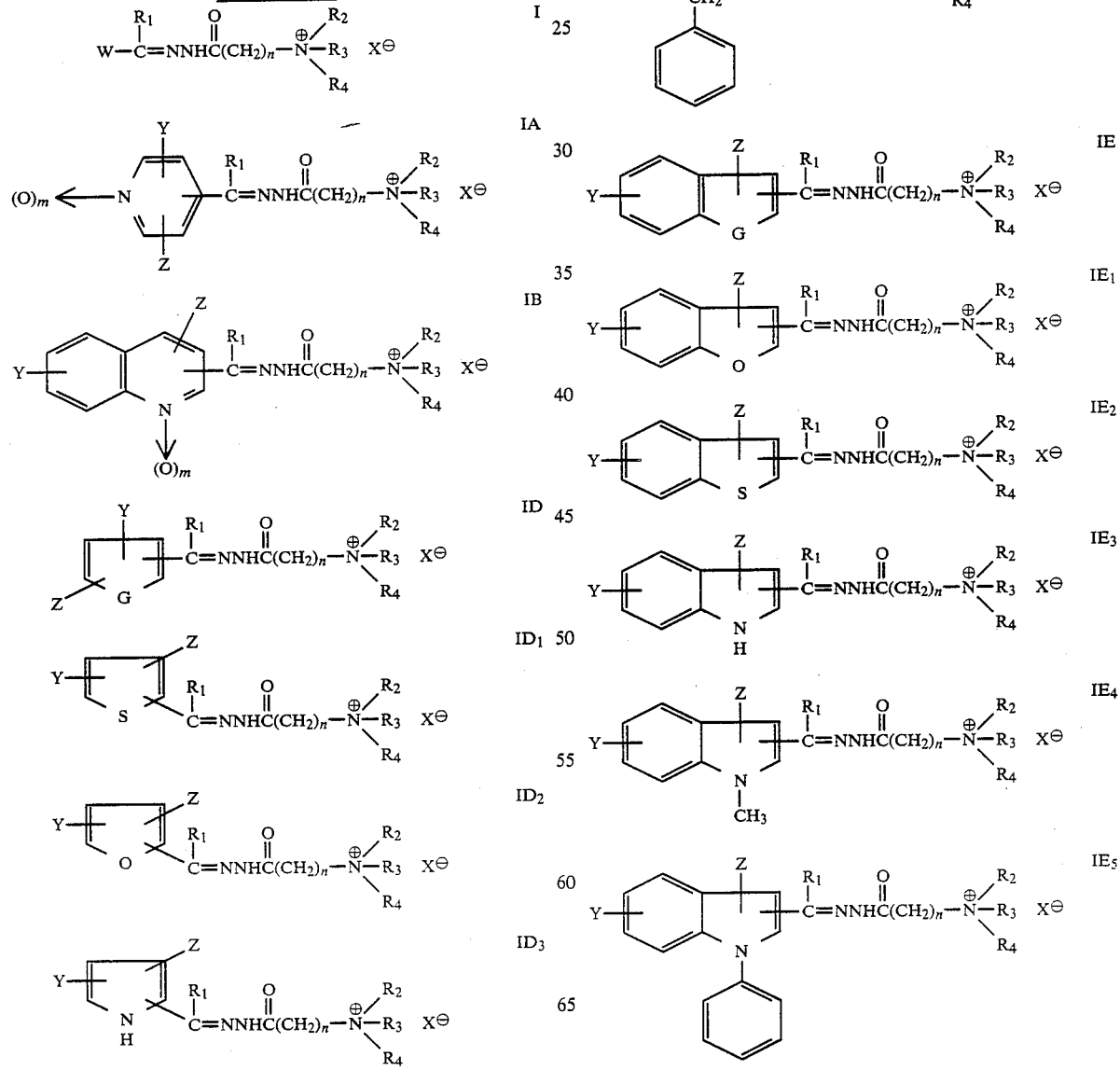

-continued
FORMULAE

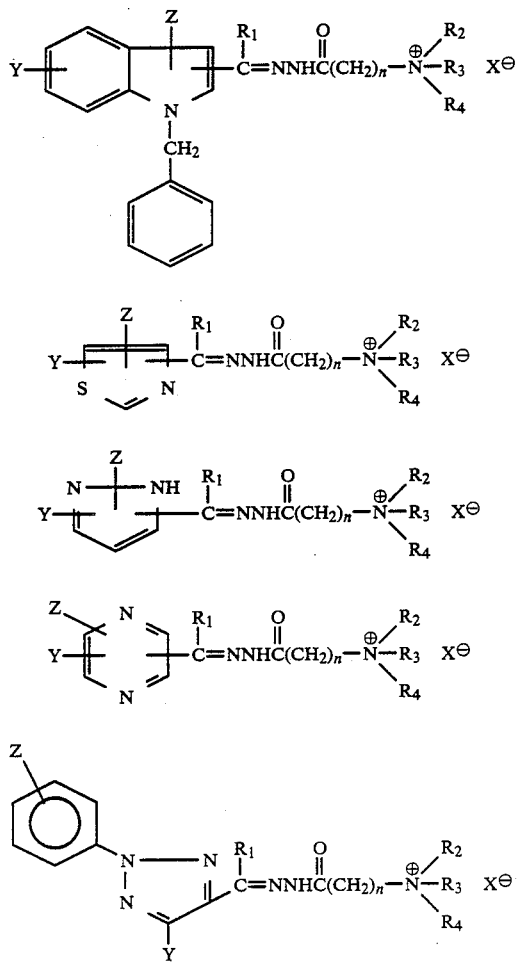

CHART A

Scheme A:

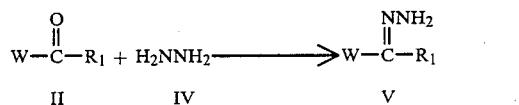

Scheme B:

-continued
CHART A

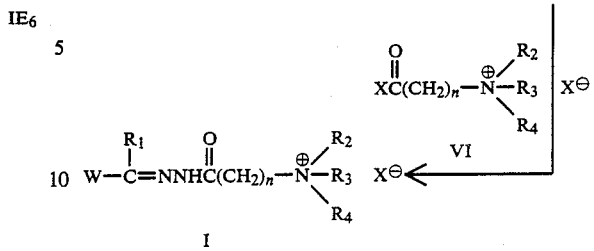

X is a halogen atom or other active group, for example, an anhydride.

Scheme C:

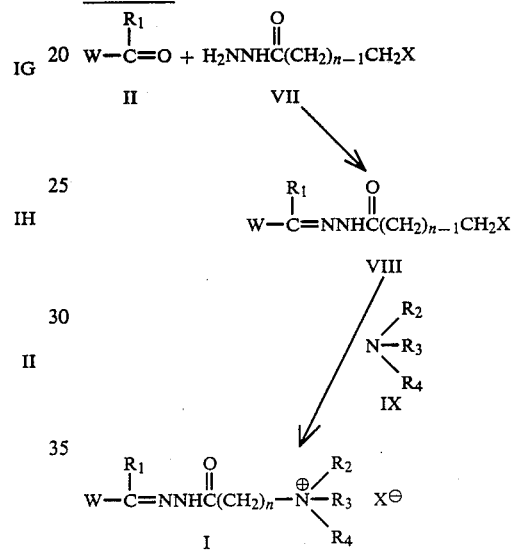

We claim:

1. A method of killing parasitic worms in humans and valuable warm-blooded domestic animal which comprises administering to humans or valuable warm-blooded domestic animals in need, a therapeutic or prophylactic dosage of a pyridinyl quaternaryalkyl acylhydrazone, hydrate thereof, or pharmaceutically acceptable salt thereof of the formula IA:

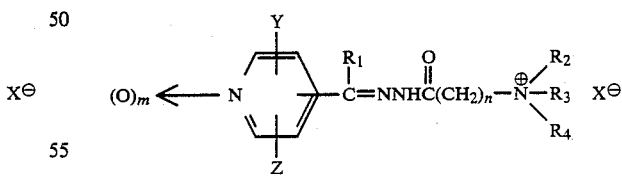

wherein X and Y, being the same or different, are selected from hydrogen, hydroxy, $C_1$-$C_4$ alkyl, $C_1$-$C_3$ alkoxy, $C_1$-$C_3$ alkylthio, halo or trifluoromethyl; with the proviso that only X or Y is hydroxy;

wherein $R_1$ is hydrogen; $C_1$-$C_4$ alkyl; cyclo($C_3$-$C_6$)alkyl optionally substituted with one, 2 or 3 $C_1$-$C_3$ alkyl; phenyl optionally substituted with one, 2 or 3 $C_1$-$C_4$ alkyl, halo, trifluoromethyl, or $C_1$-$C_3$ alkoxy; phenyl($C_1$-$C_3$)alkyl optionally substituted with one, 2 or 3 $C_1$-$C_4$ alkyl, halo, trifluoromethyl, or $C_1$-$C_3$ alkoxy, or 1,3-dioxacyclohexan-5-yl;

wherein n is 1-4;

wherein m is 0 or 1;

wherein $R_2$, $R_3$ and $R_4$ are taken together with the nitrogen to form pyridinyl optionally substituted with phenyl and/or one or two $C_1$-$C_4$ alkyl or $C_1$-$C_4$ alkoxy;

and X is a pharmaceutically acceptable anion.

2. The method of claim 1 wherein the compound of hydrate thereof is 1-[2-oxo-2-[[[2-phenyl-1-(2-pyridinyl)ethylidene]hydrazino]ethyl]-pyridinium chloride.

3. The method according to claim 1 wherein X is a halogen atom, acetate or benzenesulfonate.

4. The method according to claim 1 wherein the parasitic worms are filarae.

5. The method according to claim 1 wherein the parasitic worms are Dirolilaria.

6. A compound, hydrate thereof or pharmaceutical acceptable salt thereof of the formula IA

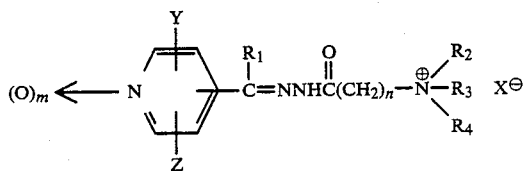

wherein X and Y, being the same or different, are selected from hydrogen, hydroxy, $C_1$-$C_4$ alkyl, $C_1$-$C_3$ alkoxy, $C_1$-$C_3$ alkylthio, halo or trifluoromethyl; with the proviso that only X or Y is hydroxy;

wherein $R_1$ is hydrogen; $C_1$-$C_4$ alkyl; cyclo($C_3$-$C_6$)alkyl optionally substituted with one, 2 or 3 $C_1$-$C_3$ alkyl; phenyl optionally substituted with one, 2 or 3 $C_1$-$C_4$ alkyl, halo, trifluoromethyl, or $C_1$-$C_3$ alkoxy; phenyl($C_1$-$C_3$)alkyl optionally substituted with one, 2 or 3 $C_1$-$C_4$ alkyl, halo, trifluoromethyl, or $C_1$-$C_3$ alkoxy, or 1,3-dioxacyclohexan-5-yl;

wherein n is 1-4;

wherein m is 0 or 1;

wherein $R_2$, $R_3$ and $R_4$ are taken together with the nitrogen to form pyridinyl optionally substituted with phenyl and/or one or two $C_1$-$C_4$ alkyl or $C_1$-$C_4$ alkoxy;

and X is a pharmaceutically acceptable anion; other than

1-[[[[1-(3-pyridinyl)ethylidene]hydrazino]carbonyl]-methyl]pyridinum chloride; or 1-[[[[1-(3-pyridinyl)ethylidene]hydrazino]carbonyl]-propyl]pyridinum chloride.

7. A compound according to claim 6 wherein the compound or hydrate thereof is 1-[2-oxo-2-[[[2-phenyl-1-(2-pyridinyl)ethylidene]hydrazino]ethyl]-pyridinium chloride.

8. An anthelmintic composition for administration to animals comprising a physiologically acceptable carrier and adjuvants, and at least an effective anthelmintic amount of a pyridinyl quaternaryalkyl acylhydrazone, hydrate thereof or pharmaceutically acceptable salt thereof of the formula IA

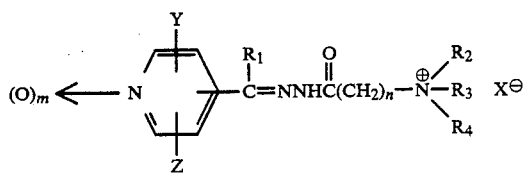

wherein X and Y, being the same or different, are selected from hydrogen, hydroxy, $C_1$-$C_4$ alkyl, $C_1$-$C_3$ alkoxy, $C_1$-$C_3$ alkylthio, halo or trifluoromethyl; with the proviso that only X or Y is hydroxy;

wherein $R_1$ is hydrogen; $C_1$-$C_4$ alkyl; cyclo($C_3$-$C_6$)alkyl optionally substituted with one, 2 or 3 $C_1$-$C_3$ alkyl; phenyl optionally substituted with one, 2 or 3 $C_1$-$C_4$ alkyl, halo, trifluoromethyl, or $C_1$-$C_3$ alkoxy; phenyl($C_1$-$C_3$)alkyl optionally substituted with one, 2 or 3 $C_1$-$C_4$ alkyl, halo, trifluoromethyl, or $C_1$-$C_3$ alkoxy, or 1,3-dioxacyclohexan-5-yl;

wherein n is 1-4;

wherein m is 0 or 1;

wherein $R_2$, $R_3$ and $R_4$ are taken together with the nitrogen to form pyridinyl optionally substituted with phenyl and/or one or two $C_1$-$C_4$ alkyl or $C_1$-$C_4$ alkoxy;

and X is a pharmaceutically acceptable anion.

* * * * *